US009782119B2

(12) United States Patent
Yamanashi et al.

(10) Patent No.: US 9,782,119 B2
(45) Date of Patent: Oct. 10, 2017

(54) WRINKLE DETECTION APPARATUS AND WRINKLE DETECTION METHOD

(71) Applicant: Panasonic Intellectual Property Management Co., Ltd., Osaka (JP)

(72) Inventors: Tomofumi Yamanashi, Kanagawa (JP); Hidekazu Araki, Fukushima (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 177 days.

(21) Appl. No.: 14/726,631

(22) Filed: Jun. 1, 2015

(65) Prior Publication Data

US 2015/0351682 A1 Dec. 10, 2015

(30) Foreign Application Priority Data

Jun. 9, 2014 (JP) ................. 2014-118506

(51) Int. Cl.
*A61B 5/02* (2006.01)
*G06K 9/00* (2006.01)
(Continued)

(52) U.S. Cl.
CPC ............ *A61B 5/442* (2013.01); *A61B 5/0077* (2013.01); *A61B 5/742* (2013.01); *G06K 9/00228* (2013.01); *G06K 9/00268* (2013.01); *G06T 7/0012* (2013.01); *G06T 7/13* (2017.01); *G06T 7/136* (2017.01); *A61B 2576/00* (2013.01);
(Continued)

(58) Field of Classification Search
USPC .......................................... 600/476; 382/128
See application file for complete search history.

(56) References Cited

U.S. PATENT DOCUMENTS

| 2011/0044515 A1* | 2/2011 | Spyridonos | G06T 7/0012 382/128 |
| 2011/0263946 A1* | 10/2011 | el Kaliouby | A61B 5/1128 600/300 |
| 2014/0205159 A1 | 7/2014 | Yoshida | |

FOREIGN PATENT DOCUMENTS

| CN | 102798343 A | 11/2012 |
| JP | 8-123967 | 5/1996 |

(Continued)

OTHER PUBLICATIONS

The Extended European Search Report dated Nov. 17, 2015 for the related European Patent Application No. 15166536.1.
(Continued)

*Primary Examiner* — Nicole F Johnson
(74) *Attorney, Agent, or Firm* — Greenblum & Bernstein, P.L.C.

(57) ABSTRACT

A wrinkle detection apparatus is an apparatus for detecting a wrinkle area of skin included in an image. The wrinkle detection apparatus includes a first threshold processing unit that detects a first edge area included in the image by performing first threshold processing for comparing a gradient value that indicates a degree of change in pixel values in the image with a first threshold, a second threshold processing unit that detects a second edge area included in the image by performing second threshold processing for comparing the gradient value with a second threshold, and an edge selection processing unit that determines a wrinkle area based on an overlapping area in which the first edge area and the second edge area are overlapped.

7 Claims, 6 Drawing Sheets

(51) Int. Cl.
*A61B 5/00* (2006.01)
*G06T 7/00* (2017.01)
*G06T 7/13* (2017.01)
*G06T 7/136* (2017.01)

(52) U.S. Cl.
CPC ............ *G06T 2207/10004* (2013.01); *G06T 2207/30088* (2013.01); *G06T 2207/30201* (2013.01)

(56) References Cited

FOREIGN PATENT DOCUMENTS

| | | |
|---|---|---|
| JP | 2009-132524 A | 6/2009 |
| JP | 2011-008643 | 1/2011 |
| JP | 2011-115460 | 6/2011 |
| WO | 2013/042436 | 3/2013 |

OTHER PUBLICATIONS

Pablo Suau Ed—Carlos Bento et al: "Adapting Hausdorff Metrics to Face Detection Systems: A Scale-Normalized Hausdorff Distance Approach", Dec. 5, 2005 (Dec. 5, 2005), Progress in Artificial Intelligence Lecture Notes in Computer Science; Lecture Notes in Artificial Intelligence; LNCS, Springer, Berlin, DE, pp. 76-86.

Xiaofeng Ren Ed—David Forsyth et al: "Multi-scale Improves Boundary Detection in Natural Images", Oct. 12, 2008 (Oct. 12, 2008), Computer Vision—ECCV 2008; [Lecture Notes in Computer Science], Springer Berlin Heidelberg, Berlin, Heidelberg, pp. 533-545.

Bernat Bas et al: "Facial Image-Based Gender and Age Estimation", Aug. 30, 2013 (Aug. 30, 2013), XP055208030, Information Coding Group Department of Electrical Engineering Linkoping University Retrieved from the Internet: URL:https://upcommons.upc.edu/bitstream/handle/2099.1/19025/Facial-Image%20Based%20Age%20and%20Gender%20Estimation.pdf?sequence=4 [retrieved on Aug. 17, 2015].

Communication pursuant to Article 94(3) EPC dated Jul. 11, 2017 for the related European Patent Application No. 15166536.1.

* cited by examiner

WRINKLE DETECTION APPARATUS AND WRINKLE DETECTION METHOD

BACKGROUND

1. Technical Field

The present disclosure relates to a wrinkle detection apparatus and a wrinkle detection method for detecting a wrinkle area of skin included in an image.

2. Description of the Related Art

Conventionally, a wrinkle area of skin is detected from a photographed face image. The wrinkle area refers to a linear image area of a wrinkle portion shown on the image.

However, the wrinkle area is not detected, or a portion that is not a wrinkle is detected as the wrinkle area in some cases under influence of illumination or the like. Therefore, PTL 1, for example, describes a technique to improve accuracy of detection (hereinafter referred to as "wrinkle detection") of the wrinkle area from the image.

The technique (hereinafter referred to as "conventional technique") described in PTL 1 calculates a gradient value in each portion of the image by using an edge detection filter, and obtains a line element from the image by comparing each gradient value with a threshold. Here, the gradient value refers to a value that indicates a degree of change in pixel values in the image. By repeating processing for comparing each gradient value with a lower threshold in a portion adjacent to the obtained line element, the conventional technique expands the area of line element.

As the threshold increases, detection (hereinafter referred to as "misdetection") of a component other than the wrinkle, such as a chloasma, is reduced. As the threshold decreases, on the other hand, failures to detect the wrinkle that actually exists (hereinafter referred to as "omission of detection") are reduced.

CITATION LIST

Patent Literatures

PTL 1: Unexamined Japanese Patent Publication No. H08-123967
PTL 2: Unexamined Japanese Patent Publication No. 2011-8643
PTL 3: Unexamined Japanese Patent Publication No. 2011-115460

SUMMARY

However, the conventional technique, which needs to repeat the processing for switching the threshold and searching a vicinity of each obtained line element, requires a high processing load. For example, when wrinkle detection is performed by following a moving image obtained by shooting a face, or when wrinkle detection is performed by using calculation capability or a battery-operated portable information processing terminal, highly accurate wrinkle detection is preferably implemented under the processing load as low as possible.

One non-limiting and exemplary aspect of the present disclosure is a wrinkle detection apparatus capable of performing highly accurate wrinkle detection under a lower processing load.

Additional benefits and advantages of one aspect of the present disclosure will be apparent from the present specification and the drawings. The benefits and/or advantages may be individually provided by various aspects and features disclosed in the present specification and the drawings, which need not all be provided in order to obtain one or more of such benefits and/or advantages.

A wrinkle detection apparatus according to the present disclosure includes: a first threshold processing unit that detects a first edge area included in an image by performing first threshold processing for comparing a gradient value that indicates a degree of change in pixel values in the image including skin with a first threshold; a second threshold processing unit that detects a second edge area included in the image by performing second threshold processing for comparing the gradient value with a second threshold; and an edge selection processing unit that determines a wrinkle area based on an overlapping area in which the first edge area and the second edge area are overlapped.

These comprehensive or specific aspects may be implemented by a system, a method, an integrated circuit, a computer program, or a computer-readable recording medium, and may be implemented by an arbitrary combination of a system, a method, an integrated circuit, a computer program, and a computer-readable recording medium. Examples of the computer-readable recording medium include a nonvolatile recording medium, such as a CD-ROM (Compact Disc-Read Only Memory).

The present disclosure enables highly accurate wrinkle detection under the lower processing load.

DETAILED DESCRIPTION OF THE PREFERRED EMBODIMENTS

Exemplary embodiments of the present disclosure will be described in detail below with reference to the drawings.

First Exemplary Embodiment

A first exemplary embodiment of the present disclosure is an example of basic aspects of the present disclosure.

<Configuration of a Wrinkle Detection Apparatus>

First, a configuration of a wrinkle detection apparatus according to the present exemplary embodiment will be described.

Figure 1:
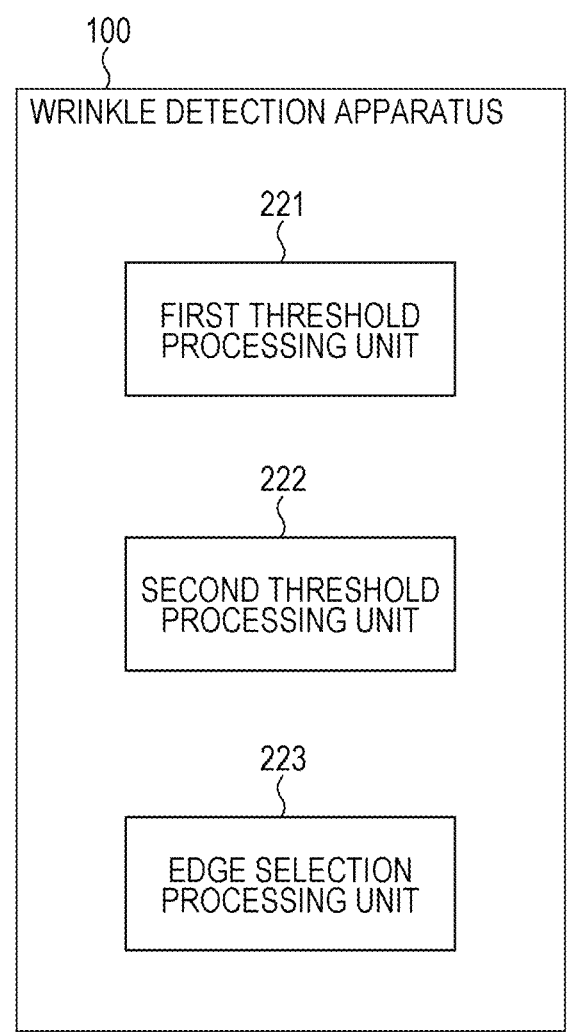
FIG. 1 is a block diagram illustrating an example of a configuration of a wrinkle detection apparatus according to a first exemplary embodiment of the present disclosure.

FIG. 1 is a block diagram illustrating an example of the configuration of the wrinkle detection apparatus according to the present exemplary embodiment.

In FIG. 1, wrinkle detection apparatus 100 is an apparatus for detecting a wrinkle area of skin included in an image, and includes first threshold processing unit 221, second threshold processing unit 222, and edge selection processing unit 223.

First threshold processing unit 221 detects a first edge area included in the image by performing first threshold processing for comparing a gradient value with a first threshold in each portion of the image. The gradient value refers to a value that indicates a degree of change in pixel values in the image, and becomes higher in an edge portion where the degree of change in pixel values is greater.

Second threshold processing unit 222 detects a second edge area included in the image by performing second threshold processing for comparing the gradient value with a second threshold in each portion of the image.

Edge selection processing unit 223 determines the wrinkle area based on an overlapping area in which the first edge area detected by the first threshold processing and the second edge area detected by the second threshold processing are overlapped.

Wrinkle detection apparatus 100 includes, for example, a CPU (Central Processing Unit), a storage medium, such as a ROM (Read Only Memory) that stores a control program, and a working memory, such as a RAM (Random Access Memory), although not illustrated. In this case, functions of the above units of wrinkle detection apparatus 100 are implemented by the CPU executing the control program.

The overlapping area is likely to be at least part of a true wrinkle area. Accordingly, wrinkle determination based on the overlapping area allows for improvement in accuracy of the wrinkle determination. In addition, processing for determining the wrinkle area based on the first threshold processing, the second threshold processing, and the overlapping area does not need to repeat the processing for searching a vicinity of a line element while switching the threshold, as in the conventional technique. Therefore, wrinkle detection apparatus 100 according to the present exemplary embodiment can perform highly accurate wrinkle detection under a lower processing load.

Second Exemplary Embodiment

A second exemplary embodiment of the present disclosure is an example of a specific aspect in a case where the present disclosure is applied to an apparatus that detects a wrinkle area of facial skin and presents the wrinkle area to a user.

Figure 2:
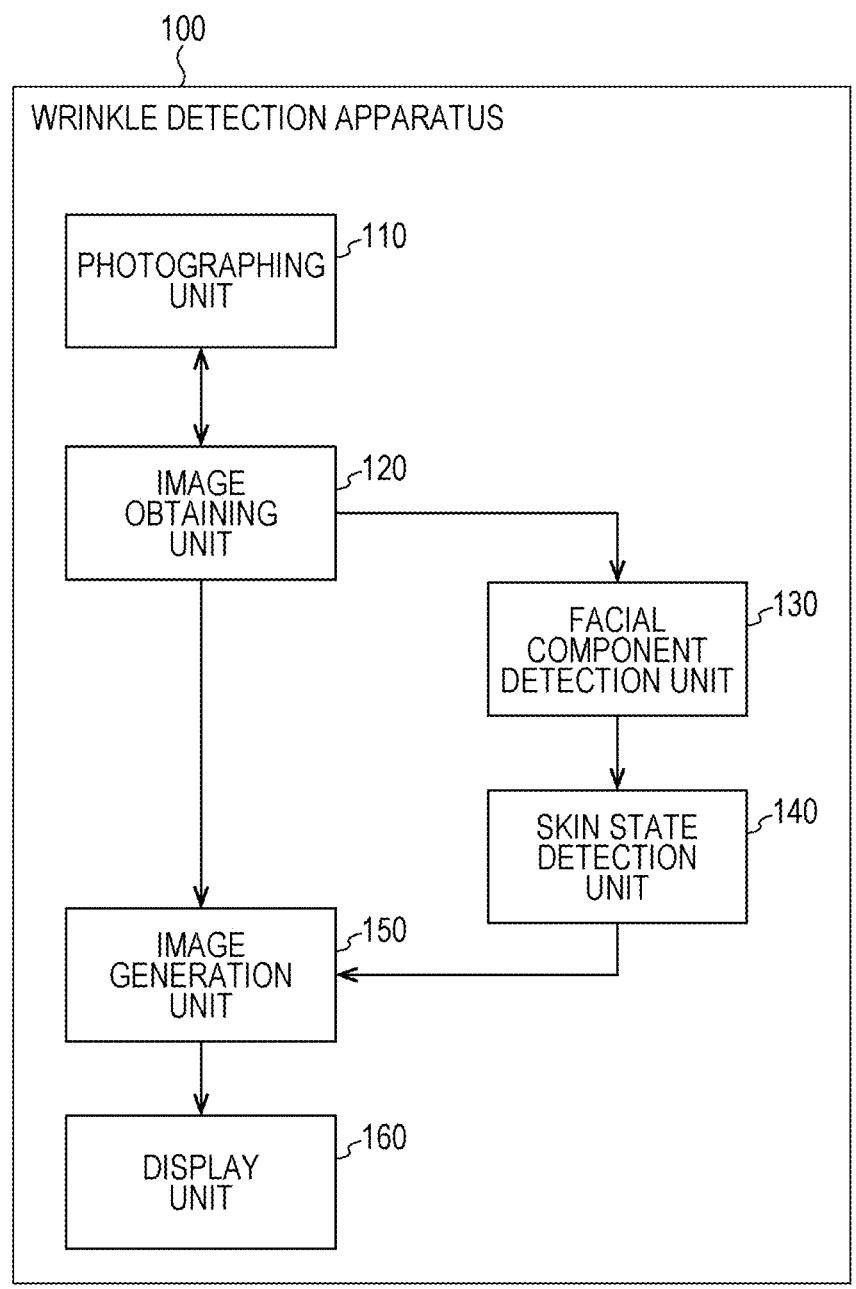
FIG. 2 is a block diagram illustrating an example of a configuration of a wrinkle detection apparatus according to a second exemplary embodiment of the present disclosure.

FIG. 2 is a block diagram illustrating an example of a configuration of wrinkle detection apparatus 100 according to the present exemplary embodiment.

In FIG. 2, wrinkle detection apparatus 100 includes photographing unit 110, image obtaining unit 120, facial component detection unit 130, skin state detection unit 140, image generation unit 150, and display unit 160.

Photographing unit 110 is, for example, a camera including a lens and a color image pickup device, and photographs an image of a user's face. Photographing unit 110 then outputs the photographed image to image obtaining unit 120. An operation of photographing unit 110 is controlled by, for example, image obtaining unit 120.

Image obtaining unit 120 performs required image quality processing, such as brightness adjustment, on the image that is input from photographing unit 110, and outputs the image to each of facial component detection unit 130 and image generation unit 150. As such image quality processing, processing suitable for edge detection processing described later is employed. In the following description, the image that is output from image obtaining unit 120 is referred to as "a photographed image."

The photographed image may be flipped horizontally by image obtaining unit 120 or another unit.

Facial component detection unit 130 detects, from the photographed image, positions of facial components in the photographed image. Each of the facial components refers to a section that constitutes a face, such as eyes, a nose, and cheeks, and can be defined, for example, by a position of a feature of the face, such as inner canthi. Facial component detection unit 130 detects the positions of the facial components by extracting the feature of the face from the photographed image, for example, by using a known image feature detection method such as pattern matching. Facial component detection unit 130 then outputs the photographed image and facial component positional information that indicates the detected positions of the respective facial components to skin state detection unit 140.

Skin state detection unit 140 detects the wrinkle area in the photographed image. Skin state detection unit 140 then outputs wrinkle area information that indicates the detected wrinkle area to image generation unit 150.

Figure 3:
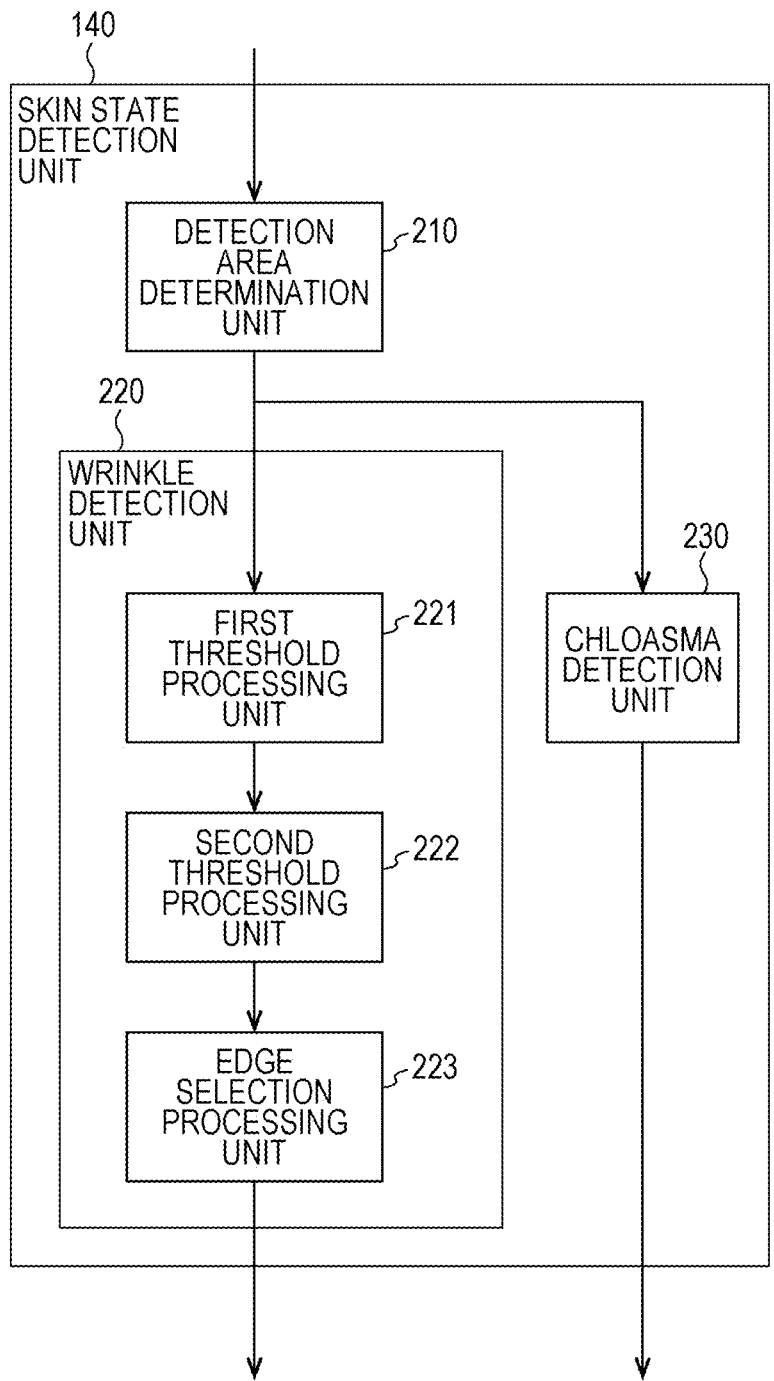
FIG. 3 is a block diagram illustrating an example of a configuration of a skin state detection unit according to the present second exemplary embodiment.

FIG. 3 is a block diagram illustrating an example of a configuration of skin state detection unit 140.

In FIG. 3, skin state detection unit 140 includes detection area determination unit 210, wrinkle detection unit 220, and chloasma detection unit 230.

Detection area determination unit 210 determines a detection area that is a target of wrinkle detection based on the facial component positional information that is input from facial component detection unit 130. For example, from positions of both eyes and a nose, detection area determination unit 210 determines an area from a lower eyelid of a left eye to a left cheek, and an area from a lower eyelid of a right eye to a right cheek as the detection area. Such an area is typically an area where wrinkles tend to appear. Detection area determination unit 210 then outputs the photographed image and detection area information that indicates the determined detection area to wrinkle detection unit 220 and chloasma detection unit 230.

Detection area determination unit 210 may exclude an area occupied by eyelashes, hair, a rim of glasses, and the like from the detection area. For example, the eyelashes area can be removed through use of a known image processing technique, such as techniques described in PTL 2 or PTL 3.

Wrinkle detection unit 220 detects the wrinkle area in the detection area. Wrinkle detection unit 220 includes first threshold processing unit 221, second threshold processing unit 222, and edge selection processing unit 223.

First threshold processing unit 221 detects an edge area included in the photographed image, through application of first threshold processing to at least the detection area indicated by the detection area information that is input from detection area determination unit 210, out of the photographed image that is input from detection area determination unit 210. First threshold processing unit 221 then outputs the photographed image, the detection area information, and first edge area information that indicates the edge area (hereinafter referred to as "a first edge area") detected by the first threshold processing, to second threshold processing unit 222.

The first threshold processing refers to processing for calculating a gradient value and comparing the calculated gradient value with a first threshold in each portion of the photographed image.

The gradient value in each portion is a value that indicates a degree of change in pixel values in the image; for example, the gradient value is a value obtained through application of a known edge detection filter to image data of the detection area. As the edge detection filter, a Gabor filter, a Laplacian filter, a Prewitt filter, a Sobel filter, and the like can be employed.

When the gradient value becomes higher as the degree of change in the corresponding pixel values becomes higher, in the first threshold processing, the area where the gradient value is equal to or greater than the first threshold is detected as the first edge area. That is, the first threshold processing is the edge detection processing using the first threshold.

Second threshold processing unit 222 detects an edge area included in the photographed image, through application of second threshold processing to at least the detection area indicated by the detection area information that is input from first threshold processing unit 221, out of the photographed image that is input from first threshold processing unit 221. Second threshold processing unit 222 then outputs the first edge area information, and second edge area information that indicates the edge area (hereinafter referred to as "a second edge area") detected by the second threshold processing, to edge selection processing unit 223.

The second threshold processing is processing similar to the first threshold processing, and detects the edge area by using the second threshold, not the first threshold. That is, the second threshold processing is the edge detection processing using the second threshold.

Here, it is assumed that the degree (gradient value) of change in pixel values corresponding to the second threshold is higher than the degree (gradient value) of change in pixel values corresponding to the first threshold. That is, the first edge area is unlikely to miss the wrinkle area compared with the second edge area. The second edge area is unlikely to include any area (hereinafter referred to as "noise") other than the wrinkle area, such as a series of pores, gloss of skin, and a chloasma, compared with the first edge area.

The edge area detected by the first threshold processing may be detected as a plurality of separated areas. In the following description, each of the plurality of separated areas is referred to as "the first edge area." That is, one first edge area is one continuous area. The first threshold processing allows for detection of the plurality of first edge areas. This also applies to "the second edge area."

An apparatus unit for calculating the gradient value of each portion of the photographed image may be disposed at an upstream stage of first threshold processing unit 221 and second threshold processing unit 222, apart from these apparatus units 221 and 222.

Edge selection processing unit 223 obtains the overlapping area in which the first edge area and the second edge area are overlapped, based on the first edge area information and the second edge area information that are input from second threshold processing unit 222. Edge selection processing unit 223 can obtain the plurality of overlapping areas. Edge selection processing unit 223 determines the wrinkle area based on the obtained overlapping area. Edge selection processing unit 223 then outputs the wrinkle area information that indicates the determined wrinkle area to image generation unit 150 (see FIG. 2). Details of wrinkle area determination will be described later.

From the photographed image that is input from area estimation unit 210, chloasma detection unit 230 detects a chloasma area of skin included in the photographed image. For example, chloasma detection unit 230 performs processing for extracting the pixel having the pixel value equal to or less than a threshold, for at least a detection area indicated by detection area information that is input, among the photographed image, by using signals of RGB channels, thereby performing such chloasma area detection. Chloasma detection unit 230 then outputs chloasma area information that indicates the detected chloasma area to image generation unit 150 (see, FIG. 2).

Based on the wrinkle area information that is input from wrinkle detection processing unit 223, image generation unit 150 of FIG. 2 generates a wrinkle image that indicates the wrinkle area in the photographed image, and generates a wrinkle-enhanced image obtained by superimposing the generated wrinkle image on the photographed image. The wrinkle image is, for example, an image for indicating a position of a wrinkle line with the wrinkle area filled with a predetermined color. Image generation unit 150 then outputs the generated wrinkle-enhanced image to display unit 160.

The wrinkle-enhanced image may be flipped horizontally by image generation unit 150 or downstream display unit 160. Image generation unit 150 may generate a chloasma image that indicates the chloasma area in the photographed image based on the chloasma area information, and may include the generated wrinkle image in the wrinkle-enhanced image.

Display unit 160 includes, for example, a liquid crystal display, and displays the wrinkle-enhanced image that is input from image generation unit 150.

Wrinkle detection apparatus 100 includes, for example, a CPU, a storage medium such as a ROM that stores a control program, and a working memory such as a RAM, although not illustrated. In this case, functions of the above units of wrinkle detection apparatus 100 are implemented by the CPU executing the control program.

Wrinkle detection apparatus 100 having such a configuration can perform wrinkle determination based on the overlapping area in which the first edge area based on the first threshold and the second edge area based on the second threshold are overlapped. Wrinkle detection apparatus 100 can then present a determination result to a user.

<Determination of the Wrinkle Area>

A determination method of the wrinkle area in edge selection processing unit 223 and its significance will now be described.

Figure 4:
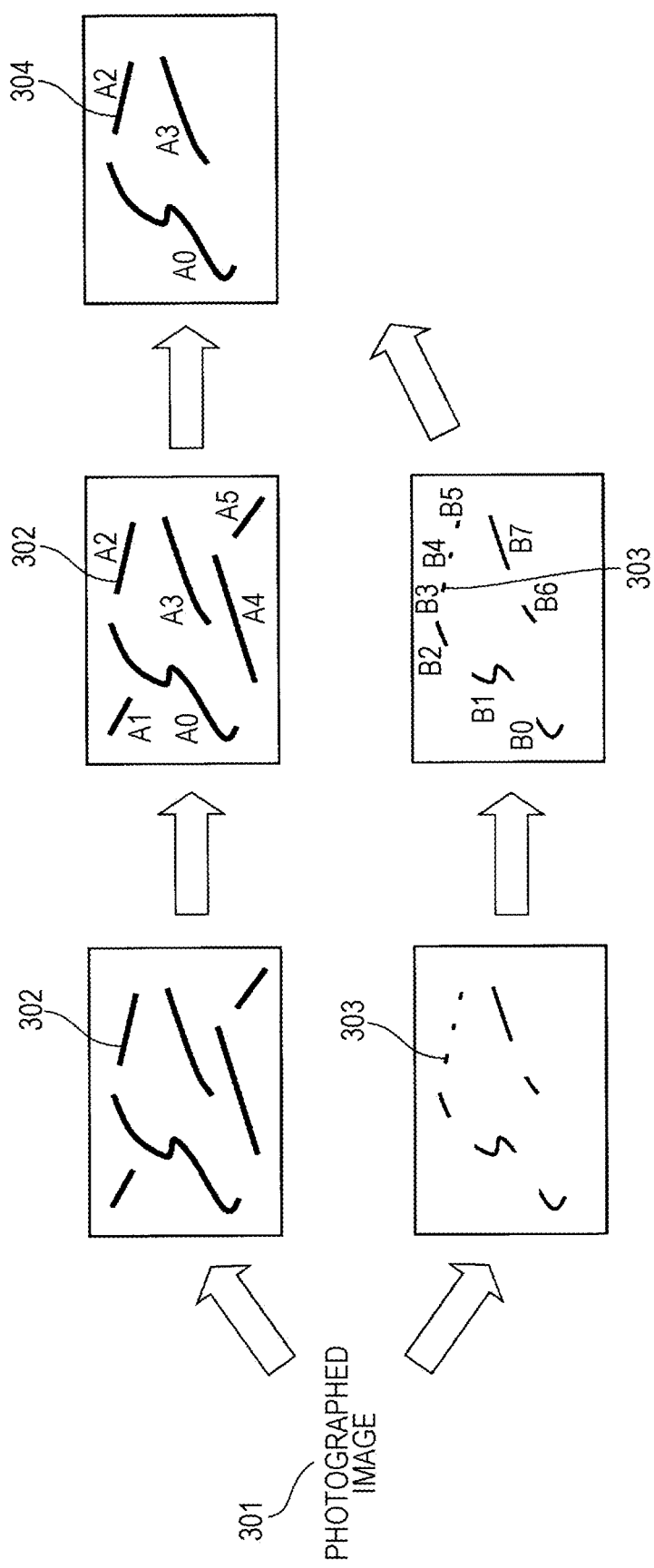
FIG. 4 is a diagram for illustrating an example of a determination method of a wrinkle area according to the present second exemplary embodiment.

FIG. 4 is a diagram for illustrating an example of the determination method of the wrinkle area.

As illustrated in FIG. 4, it is assumed that application of the first threshold processing and the second threshold processing to photographed image (detection area) 301 causes detection of a plurality of first edge areas 302 and a plurality of second edge areas 303. As described above, first edge area 302 has lower criteria of edge detection. Accordingly, more areas will be detected as first edge area 302, compared with second edge area 303.

Edge selection processing unit 223 performs, for example, labeling processing for labeling each of the plurality of first edge areas 302 as A0, A1, . . . , A5. In addition, edge selection processing unit 223 performs, for example, labeling processing for labeling each of the plurality of second edge areas 303 as B0, B1, . . . , B7.

Although first edge areas 302 are likely to include more wrinkle areas, first edge areas 302 are also likely to include noise. Meanwhile, when at least part of first edge area 302, which is a cluster of continuous edge area, is the true wrinkle area, all of pertinent first edge area 302 is likely to be the true wrinkle area.

Second edge areas 303 are unlikely to include noise. Accordingly, all of second edge areas 303 are likely to be the true wrinkle areas.

Therefore, edge selection processing unit 223 selects first edge area 302 including at least part of second edge area 303 out of one or more first edge areas 302 as the wrinkle area. In other words, edge selection processing unit 223 selects first edge area 302 including the overlapping area in which first edge area 302 and second edge area 303 are overlapped out of first edge areas 302 as the wrinkle area.

Specifically, edge selection processing unit 223 extracts an area obtained by deleting first edge area 302 that does not include the overlapping area from one or more first edge areas 302 as wrinkle area 304.

In the example illustrated in FIG. 4, first edge area 302 of A0 overlaps with second edge areas 303 of B0 to B2. First edge area 302 of A2 overlaps with second edge areas 303 of B3 to B5. First edge area 302 of A3 overlaps with second edge areas 303 of B6 and B7. However, first edge areas 302 of A1, A4, and A5 do not overlap with any second edge area 303. Therefore, first edge areas 302 of A0, A2, and A3 are extracted as wrinkle areas 304.

By extracting wrinkle areas 304 in this manner, wrinkle detection apparatus 100 can perform wrinkle detection while reducing both omission of detection and misdetection.

<Operation of the Wrinkle Detection Apparatus>

Next, an operation of wrinkle detection apparatus 100 will be described.

Figure 5:
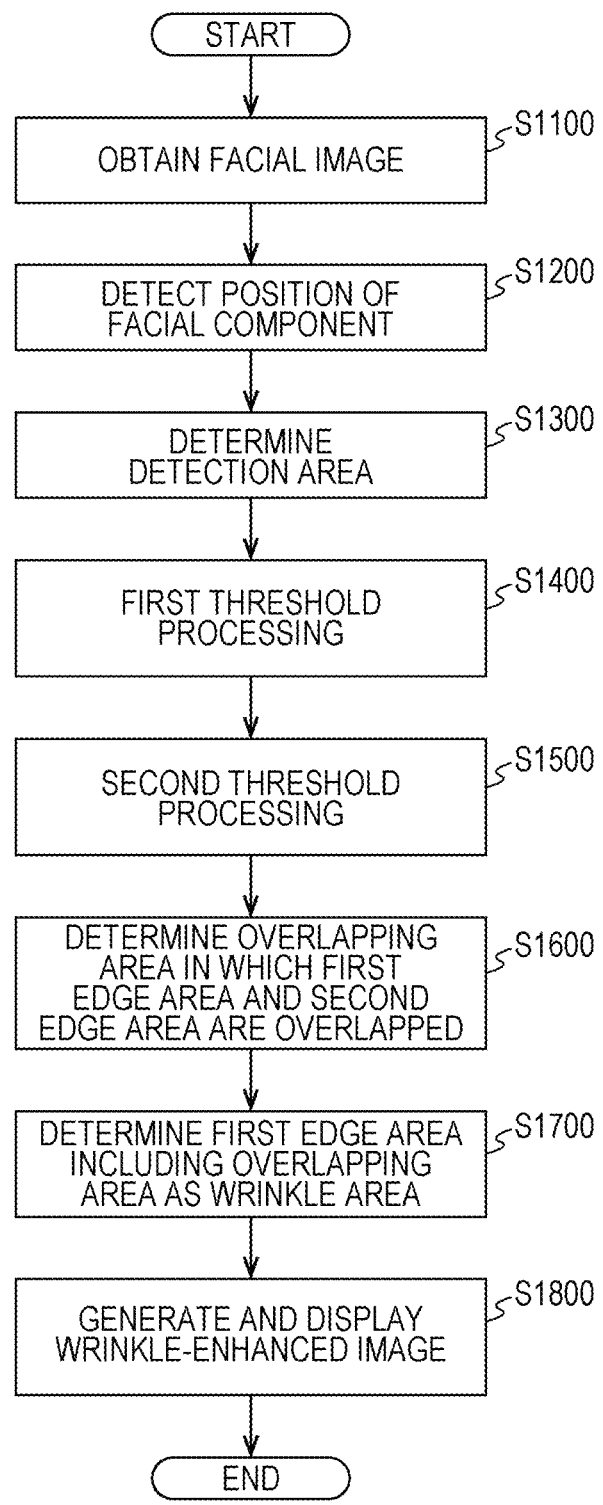
FIG. 5 is a flow chart illustrating an example of an operation of the wrinkle detection apparatus according to the present second exemplary embodiment.

FIG. 5 is a flow chart illustrating an example of the operation of wrinkle detection apparatus 100.

In step S1100, image obtaining unit 120 obtains the photographed image of the user's face by using photographing unit 110.

In step S1200, facial component detection unit 130 detects the position of each facial component from the photographed image.

In step S1300, detection area determination unit 210 determines the detection area based on the position of the facial component. The detection area is, for example, an area from a lower eyelid of a left eye to a left cheek, and an area from a lower eyelid of a right eye to a right cheek, as described above.

In step S1400, first threshold processing unit 221 applies the first threshold processing to the detection area, and detects the first edge area.

In step S1500, second threshold processing unit 222 applies the second threshold processing to the detection area, and detects the second edge area. Processing of step S1400 and processing of step S1500 may be performed in an opposite order.

In step S1600, edge selection processing unit 223 determines the overlapping area in which the first edge area and the second edge area are overlapped.

Specifically, edge selection processing unit 223 determines, for example, whether each pixel of the first edge area constitutes the second edge area.

In step S1700, edge selection processing unit 223 determines the first edge area including the overlapping area as the wrinkle area. In addition, chloasma detection unit 230 detects the chloasma area.

In step S1800, image generation unit 150 generates the wrinkle-enhanced image, and displays the wrinkle-enhanced image by using display unit 160.

Figure 6A:
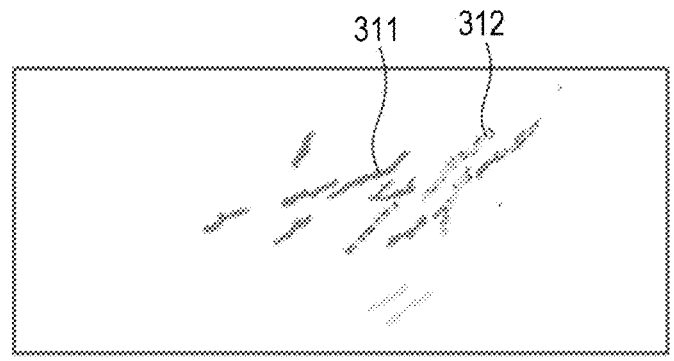
FIG. 6A is a diagram illustrating an example of how the wrinkle area is extracted according to the present second exemplary embodiment.
Figure 6B:
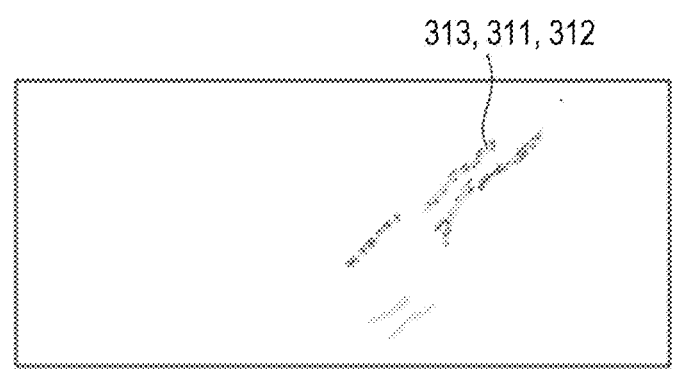
FIG. 6B is a diagram illustrating an example of how the wrinkle area is extracted according to the present second exemplary embodiment.
Figure 6C:
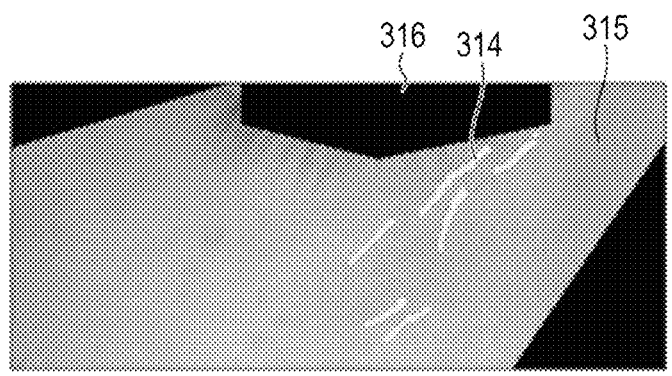
FIG. 6C is a diagram illustrating an example of how the wrinkle area is extracted according to the present second exemplary embodiment.

FIG. 6A, FIG. 6B, and FIG. 6C are diagrams each illustrating an example of how the wrinkle area is extracted.

As illustrated in FIG. 6A, part of first edge areas 311 (areas illustrated in a deep color) overlaps with second edge areas 312 (areas illustrated in a light color), while the other part of first edge areas 311 does not overlap with second edge areas 312. First edge area 311 that overlaps with second edge area 312 is likely to be the true wrinkle area, while first edge area 311 that does not overlap with second edge area 312 is likely to be noise.

Therefore, as illustrated in FIG. 6B, edge selection processing unit 223 determines, as wrinkle area 313, an area obtained by excluding first edge area 311 that does not overlap with second edge area 312 from many first edge areas 311. Then, as illustrated in FIG. 6C, wrinkle-enhanced image 316 is generated through superimposition of image 314 of wrinkle area 313 determined by edge selection processing unit 223 on photographed image 315.

When the second edge area is extracted by using parameters (for example, a wavelength in a case of the Gabor filter) other than the threshold of the gradient value of pixels, a portion that does not overlap with the first edge area can exist. In such a case, edge selection processing unit 223 may also determine such a portion as the wrinkle area. In this case, wrinkle detection can be performed in a state where omission of detection is further reduced. However, as described above, the processing load can be reduced more in the processing for determining, as the wrinkle area, an area obtained by deleting the first edge area that does not include the overlapping area from the one or more first edge areas.

The aforementioned operation allows wrinkle detection apparatus 100 to perform wrinkle determination based on the overlapping area in which the first edge area based on the first threshold and the second edge area based on the second threshold are overlapped, and to present the determination result to the user.

Wrinkle detection apparatus 100 may further perform edge detection processing using a method stricter than an extraction method of the second edge area, and may use an obtained third edge area to increase or decrease the wrinkle area. For example, wrinkle detection apparatus 100 determines that the first edge area that does not include the third edge area is not the wrinkle area, and adds the third edge area that is not included in the first edge area to the wrinkle area.

Effect of the Present Exemplary Embodiment

As described above, wrinkle detection apparatus 100 according to the present exemplary embodiment performs wrinkle determination based on the overlapping area in which the first edge area based on the first threshold and the second edge area based on the second threshold are overlapped.

The overlapping area is likely to be at least part of the true wrinkle area, as described above. Therefore, wrinkle determination based on the overlapping area allows for improvement in accuracy of wrinkle determination. In addition, wrinkle detection apparatus 100 according to the present exemplary embodiment does not need to repeat processing for searching a vicinity of a line element while switching the threshold, as in the conventional technique. Therefore, wrinkle detection apparatus 100 according to the present exemplary embodiment allows for highly accurate wrinkle detection under a lower processing load.

Variations of the Present Exemplary Embodiment

The determination method of the wrinkle area based on the overlapping area is not limited to the above example. For example, edge selection processing unit 223 may select the second edge area with at least part of the second edge area being included in the first edge area out of the second edge areas, and may determine the area obtained through interpolation between the plurality of selected second edge areas as the wrinkle area.

Although the exemplary embodiments described above assume that the detection target is the wrinkle of skin, the detection target may be another state that has a shape of a linear groove, such as a scratch on a wall, a crack on a surface of a metallic material, and a wrinkle of cloth.

SUMMARY OF THE PRESENT DISCLOSURE

A wrinkle detection apparatus according to the present disclosure includes: a first threshold processing unit that detects a first edge area included in an image by performing first threshold processing for comparing a gradient value that indicates a degree of change in pixel values in the image including skin with a first threshold; a second threshold processing unit that detects a second edge area included in the image by performing second threshold processing for comparing the gradient value with a second threshold; and an edge selection processing unit that determines a wrinkle area based on an overlapping area in which the first edge area and the second edge area are overlapped.

In the wrinkle detection apparatus, the second threshold may be larger than the first threshold, and the edge selection processing unit may select the first edge area including the overlapping area out of the one or more first edge areas as the wrinkle area.

In the wrinkle detection apparatus, the edge selection processing unit may select an area other than the first edge area that does not include the overlapping area, out of the one or more first edge areas, as the wrinkle area.

The wrinkle detection apparatus may further include: an image obtaining unit that obtains the image; a facial component obtaining unit that obtains a position of a facial component from the image; and a detection area determination unit that determines a detection area that is a target of the first threshold processing and the second threshold processing out of the image, based on the position of the facial component. The first threshold processing unit and the second threshold processing unit may calculate at least the gradient value of the detection area.

The wrinkle detection apparatus may further include: an image obtaining unit that obtains the image; an image generation unit that generates a wrinkle image indicating the wrinkle area in the image, and generates a wrinkle-enhanced image obtained through superimposition of the generated wrinkle image on the image; and a display unit that displays the wrinkle-enhanced image.

A wrinkle detection method according to the present disclosure includes: detecting a first edge area included in an image by performing first threshold processing for comparing a gradient value that indicates a degree of change in pixel values in the image including skin with a first threshold; detecting a second edge area included in the image by performing second threshold processing for comparing the gradient value with a second threshold; and determining a wrinkle area based on an overlapping area in which the first edge area and the second edge area are overlapped.

The present disclosure is useful as the wrinkle detection apparatus and the wrinkle detection method that allow for highly accurate wrinkle detection under a lower processing load.

What is claimed is:

1. A wrinkle detection apparatus comprising:
a first threshold processor adapted to detect one or more first edge areas included in an image of skin, and adapted for comparing a gradient value that indicates a degree of change in pixel values in the image with a first threshold, each of the one or more first edge areas being a continuous area in the image where the gradient value is larger than the first threshold;
a second threshold processor adapted to detect one or more second edge areas included in the image, and adapted for comparing the gradient value with a second threshold that is larger than the first threshold, each of the one or more second edges areas being another continuous area in the image where the gradient value is larger than the second threshold; and
an edge selection processor adapted for determining at least one first edge area from among the one or more first edge areas as a wrinkle area in the image, the at least one first edge area partially overlapping with at least one of the one or more second edge areas.

2. The wrinkle detection apparatus according to claim 1, further comprising:
an image obtaining unit that obtains the image;
a facial component detector that obtains a position of a facial component from the image; and
a detection area determination unit that determines a detection area that is a target of first threshold processing and second threshold processing, out of the image, based on the position of the facial component,
wherein the first threshold processor and the second threshold processor calculate at least the gradient value of the detection area.

3. The wrinkle detection apparatus according to claim 1, further comprising:
an image obtaining unit that obtains the image;
an image generation unit that generates a wrinkle image indicating the wrinkle area in the image, and generates a wrinkle-enhanced image obtained through superimposition of a generated wrinkle image on the image; and
a display that displays the wrinkle-enhanced image.

4. A wrinkle detection method comprising:
detecting one or more first edge areas included in an image of skin by comparing a gradient value that indicates a degree of change in pixel values in the image with a first threshold, each of the one or more first edge areas being a continuous area in the image where the gradient value is larger than the first threshold;
detecting one or more second edge areas included in the image by comparing the gradient value with a second threshold that is larger than the first threshold, each of the one or more second edge areas being another continuous area in the image where the gradient value is larger than the second threshold; and
determining at least one first edge area from among the one or more first edge areas as a wrinkle area in the image, the at least one first edge area partially overlapping with at least one of the one or more second edge areas.

5. A wrinkle detection apparatus comprising:
a processor; and
a memory having instructions stored thereon, the instructions when executed causing the processor to perform operations including:
- detecting one or more first edge areas included in an image of skin by comparing a gradient value that indicates a degree of change in pixel values in the image with a first threshold, each of the one or more first edge areas being a continuous area in the image where the gradient value is larger than the first threshold;
- detecting one or more second edge areas included in the image by comparing the gradient value with a second threshold that is larger than the first threshold, each of the one or more second edge areas being another continuous area in the image where the gradient value is larger than the second threshold; and
- determining at least one first edge area from among the one or more first edge areas as a wrinkle area in the image, the at least one first edge area partially overlapping with at least one or more second edge areas.

6. The wrinkle detection apparatus of claim 5, wherein the operations further include:
- obtaining the image;
- obtaining a position of a facial component from the image;
- determining a detection area that is a target of first threshold processing and second threshold processing, out of the image, based on the position of the facial component; and
- calculating at least the gradient value of the detection area.

7. The wrinkle detection apparatus of claim 5, wherein the operations further include:
- obtaining the image;
- generating a wrinkle image indicating the wrinkle area in the image, and generating a wrinkle-enhanced image obtained through superimposition of a generated wrinkle image on the image; and
- displaying the wrinkle-enhanced image.

* * * * *